(12) United States Patent
Fujii et al.

(10) Patent No.: US 7,203,279 B2
(45) Date of Patent: Apr. 10, 2007

(54) RADIOGRAPHIC APPARATUS, AND RADIATION DETECTION SIGNAL PROCESSING METHOD

(75) Inventors: Keiichi Fujii, Kyoto-fu (JP); Shoichi Okamura, Nara-ken (JP); Susumu Adachi, Osaka-fu (JP); Shinya Hirasawa, Kyoto-fu (JP); Toshinori Yoshimuta, Osaka-fu (JP); Koichi Tanabe, Kyoto-fu (JP); Shigeya Asai, Kyoto-fu (JP); Akihiro Nishimura, Kyoto-fu (JP)

(73) Assignee: Shimadzu Corporation (JP)

( * ) Notice: Subject to any disclaimer, the term of this patent is extended or adjusted under 35 U.S.C. 154(b) by 134 days.

(21) Appl. No.: 11/087,555

(22) Filed: Mar. 24, 2005

(65) Prior Publication Data

US 2005/0220268 A1    Oct. 6, 2005

(30) Foreign Application Priority Data

Mar. 31, 2004    (JP)    ............................ 2004-104838

(51) Int. Cl.
*H05G 1/58*    (2006.01)

(52) U.S. Cl. ........................ 378/116; 378/19; 378/98.8

(58) Field of Classification Search ................... 378/19, 378/62, 98.8, 114, 116, 207; 250/370.08, 250/370.09
See application file for complete search history.

(56) References Cited

FOREIGN PATENT DOCUMENTS

JP    2003-198937 A1    7/2003

*Primary Examiner*—Courtney Thomas
(74) *Attorney, Agent, or Firm*—Rader, Fishman & Grauer PLLC

(57) ABSTRACT

In the radiographic apparatus according to this invention, when a radiographic mode designator 16 designates a non-standard radiographic mode, a signal corrector 15 uses defect information stored in one of non-standard image defect information memories 18B–18E for correcting X-ray detection signals outputted from an FPD 2. Since the pixel defect information for non-standard X-ray images is acquired by a pixel defect information converter 19 through a conversion from defect information for standard X-ray images stored in a standard image defect information memory 18A, it is unnecessary to collect output signals for pixel defect information acquisition from the FPD 2 all over again. As a result, abnormal X-ray detection signals due to defects of radiation detecting elements may be corrected promptly, regardless of how the radiation detecting elements are assigned to the pixels in the X-ray images.

19 Claims, 7 Drawing Sheets

2 × 2 mini matrix

4 × 4 mini matrix

RADIOGRAPHIC APPARATUS, AND RADIATION DETECTION SIGNAL PROCESSING METHOD

BACKGROUND OF THE INVENTION (1) Field of the Invention

This invention relates to a radiographic apparatus and a radiation detection signal processing method, based on radiation detection signals outputted from a radiation detector having numerous radiation detecting elements arranged in a two-dimensional matrix, for selectively acquiring desired images from among a plurality of radiographic images with the radiation detecting elements of the radiation detector assigned differently to the pixels of the radiographic images. More particularly, the invention relates to a technique for correcting abnormal radiation detection signals due to defects of the radiation detecting elements in the radiation detector.

(2) Description of the Related Art

A medical X-ray imaging apparatus (radiographic apparatus) includes a flat panel type two-dimensional radiation detector (hereinafter called "FPD" as appropriate) acting as a radiation detector for detecting transmitted X-ray images of a patient. As shown in FIG. 8, the FPD 2 has radiation detecting elements D arranged in a two-dimensional matrix of M rows and N columns, and thus M×N detecting elements D, on a radiation detecting surface to which the transmitted X-ray images of the patient are projected. Based on X-ray detection signals outputted from the FPD 2 as a result of X-ray emission to the patient to be radiographed, as shown in FIG. 9, an X-ray image P is created with m×n pixels Q arranged in a two-dimensional matrix of m rows and n columns, to be displayed on the screen of an image display monitor, for example.

On the one hand, the FPD 2, although lightweight and thin compared with an image intensifier, inevitably includes defective radiation detecting elements D resulting from a manufacturing process or the like. X-ray detection signals corresponding to the defective radiation detecting elements D are abnormal signals without proper pixel values (signal strength), and will produce defective pixels in the X-ray image P. Thus, the abnormal X-ray detection signals are corrected in real time by replacing the pixel values of each abnormal X-ray detection signal with the pixel values of surrounding normal X-ray detection signals, or with interpolation values calculated by using the pixel values of normal X-ray detection signals adjacent each abnormal signal. Such a technique is disclosed in Japanese Unexamined Patent Publication No. 2003-198937, for example.

On the other hand, a conventional X-ray imaging apparatus can provide, as X-ray images P, not only standard X-ray images but non-standard X-ray images different from he standard X-ray images.

The "standard X-ray image" refers to an image having pixels Q (i, j) arranged in the same two-dimensional matrix as the radiation detecting elements D, with the radiation detecting elements D (I, J) assigned in a one-to-one relationship to the pixels Q (i, j). For a standard X-ray image, M=m and N=n. The "non-standard X-ray image" refers to an image having pixels Q (i, j) to which the radiation detecting elements D (I, J) of the radiation detector are assigned differently from the standard X-ray image.

A non-standard X-ray image may, for example, be a foursome cluster X-ray image having four radiation detecting elements D in a 2×2 mini matrix arrangement of two rows and two columns assigned to each pixel Q (i, j). Another non-standard X-ray image may be an X-ray image of ¾ limited matrix having radiation detecting elements D in a center matrix range of (¾) M×(¾) N assigned to the respective pixels Q (i, j).

However, the conventional X-ray imaging apparatus noted above often fails to correct promptly the abnormal X-ray detection signals due to defects of the radiation detecting elements D.

When acquiring a standard X-ray image, abnormal X-ray detection signals to be corrected are known immediately and corrected promptly since the defects of radiation detecting elements D are stored in advance as defect information corresponding to the pixels Q in the standard X-ray image. However, for a non-standard X-ray image having pixels Q to which the radiation detecting elements D are assigned differently from the standard X-ray image, the defects of radiation detecting elements D are not stored in advance as defect information corresponding to the pixels Q. It is therefore necessary to collect output signals from the FPD 2 for defect information acquisition first, and then to check the presence or absence of defects in the radiation detecting elements D. As a result, when acquiring non-standard X-ray images, abnormal X-ray detection signals cannot be corrected promptly.

SUMMARY OF THE INVENTION

This invention has been made having regard to the state of the art noted above, and its object is to provide a radiographic apparatus and a radiation detection signal processing method capable of promptly correcting abnormal radiation detection signals due to defects of radiation detecting elements, regardless of how the radiation detecting elements are assigned to the pixels of radiographic images.

The above object is fulfilled, according to this invention, by a radiographic apparatus having (A) a radiation emitting device for emitting radiation to an object to be radiographed, and (B) a two-dimensional radiation detector with a plurality of radiation detecting elements arranged in a two-dimensional matrix, the apparatus comprising (C) a radiographic mode designating device for selectively designating a standard radiographic mode for acquiring standard radiographic images, and a non-standard radiographic mode for acquiring non-standard radiographic images; (D) a standard image defect information storage device for storing pixel defect information for standard images; (E) a pixel defect information converting device for performing a conversion process to convert the pixel defect information for standard images stored in the standard image defect information storage device into pixel defect information for non-standard images; and (F) a signal correcting device for correcting radiation detection signals according to the pixel defect information for standard images when the standard radiographic mode is designated by the radiographic mode designating device, and according to the pixel defect information for non-standard images when the non-standard radiographic mode is designated by the radiographic mode designating device; wherein the standard radiographic images are images each having a plurality of pixels arranged in the same two-dimensional matrix as the radiation detecting elements, with the radiation detecting elements assigned in a one-to-one relationship to the pixels; the non-standard radiographic images are images for which the radiation detecting elements are assigned to pixels differently from the standard radiographic mode; the pixel defect information for standard images is defect information containing, in an element-to-pixel relationship, presence or absence of defects in the radiation detecting elements corresponding to the respective pixels of the standard radiographic images; the pixel defect information for non-standard images is defect information containing, in an element-to-pixel relationship, presence or absence of defects in the radiation detecting elements corresponding to the respective pixels of the non-standard radiographic images; and the conversion process by the pixel defect information converting device for conversion into the pixel defect information for non-standard images includes a defect determining process for checking, based on the pixel defect information for standard images stored in the standard image defect information storage device, whether even one defective radiation detecting element is present among the detecting elements assigned to the pixels of the non-standard radiographic images, and determining pixels with even one defective detecting element assigned thereto to be"defective", and pixels with no defective detecting element assigned thereto to be"defectless".

With the radiographic apparatus according to this invention, when the standard radiographic mode is designated by the radiographic mode designating device, the signal correcting device corrects, according to the pixel defect information for standard images, the radiation detection signals relating to defective radiation detecting elements among the signals outputted from the two-dimensional radiation detector in response to an emission of radiation from the radiation emitting device to the object, thereby acquiring standard radiographic images without defective pixels.

The"pixel defect information for standard images" refers to defect information containing, in an element-to-pixel relationship, the presence or absence of defects in the radiation detecting elements corresponding to the respective pixels of standard radiographic images. The "standard radiographic images" are images each having a plurality of pixels arranged in the same two-dimensional matrix as the radiation detecting elements, with the radiation detecting elements assigned in a one-to-one relationship to the pixels. The"standard radiographic mode" refers to a mode for acquiring the standard radiographic images described above.

On the other hand, when the non-standard radiographic mode is designated by the radiographic mode designating device, the signal correcting device corrects, according to the pixel defect information for non-standard images, the radiation detection signals relating to defective radiation detecting elements among the signals outputted from the two-dimensional radiation detector in response to an emission of radiation from the radiation emitting device to the object, thereby acquiring non-standard radiographic images without defective pixels.

The"pixel defect information for non-standard images" refers to defect information containing, in an element-to-pixel relationship, the presence or absence of defects in the radiation detecting elements corresponding to the respective pixels of non-standard radiographic images. The "non-standard radiographic images" are images each having pixels to which the radiation detecting elements are assigned differently from the standard radiographic mode. The "non-standard radiographic mode" refers to a mode for acquiring the non-standard radiographic images described above.

The pixel defect information for non-standard images used in correcting the radiation detection signals for non-standard radiographic images is obtained from the pixel defect information for non-standard images through the following conversion process.

The pixel defect information converting device converts the pixel defect information for standard images by checking, based on the pixel defect information for standard images, whether even one defective radiation detecting element is present among the detecting elements assigned to the pixels of the non-standard radiographic images, and determining pixels with even one defective detecting element assigned thereto to be "defective", and pixels with no defective detecting element assigned thereto to be "defectless".

Since the pixel defect information for non-standard images is converted from the pixel defect information for standard images through the conversion process as described above, it is unnecessary to collect output signals for pixel defect information acquisition for non-standard radiographic images from the two-dimensional radiation detector all over again.

That is, in the radiographic apparatus according to this invention, when the standard radiographic mode is designated, the signal correcting device corrects abnormal radiation detection signals, due to defects of the radiation detecting elements, among the radiation detection signals outputted from the two-dimensional radiation detector. This correction is carried out according to the pixel defect information for standard images stored in the standard image defect information storage device.

When the non-standard radiographic mode is designated, the signal correcting device corrects abnormal radiation detection signals, due to defects of the radiation detecting elements, among the radiation detection signals outputted from the two-dimensional radiation detector. This correction is carried out according to the pixel defect information for non-standard images converted from the pixel defect information for standard images by the pixel defect information converting device.

With the above correcting arrangement, the defect information for non-standard radiographic images is acquired by using the defect information for standard radiographic images. Thus, there is no need to collect output signals for the pixel defect information acquisition for non-standard images from the two-dimensional radiation detector all over again.

As a result, also when acquiring the non-standard radiographic image, abnormal radiation detection signals due to defects of the radiation detecting elements are corrected promptly.

With the radiographic apparatus according to this invention, therefore, abnormal radiation detection signals due to defects of the radiation detecting elements are corrected promptly regardless of how the radiation detecting elements are assigned to the pixels of radiographic images.

Preferably, the radiographic apparatus according to this invention, further comprises (G) a non-standard image defect information storage device for storing the pixel defect information for non-standard images resulting from the conversion process by the pixel defect information converting device, wherein the signal correcting device is arranged to correct the radiation detection signals according to the pixel defect information for non-standard images stored in the non-standard image defect information storage device.

In this example, the pixel defect information for non-standard images for use in correcting radiation detection signals for non-standard radiographic images is stored in the non-standard image defect information storage device. Such pixel defect information for non-standard images may be used without converting the pixel defect information for standard images into pixel defect information for non-standard images. This further speeds up the correction of abnormal radiation detection signals.

Where the apparatus includes the non-standard image defect information storage device, one preferred example is such that, after the pixel defect information for standard images is stored in the standard image defect information storage device, the pixel defect information converting device may perform the conversion process to the pixel defect information for non-standard images, and the pixel defect information for non-standard images may be stored in the non-standard image defect information storage device, for all of the non-standard radiographic images.

Where the apparatus includes the non-standard image defect information storage device, another preferred example is such that, after the radiographic mode designating device designates the non-standard radiographic mode, only the pixel defect information for non-standard images relating to the non-standard radiographic mode designated may be stored in the non-standard image defect information storage device.

The following functional effect is produced by the former example where the conversion process to the pixel defect information for non-standard images and storing of the pixel defect information for non-standard images in the non-standard image defect information storage device are performed for all of the non-standard radiographic images. That is, after the pixel defect information for standard images is stored in the standard image defect information storage, the pixel defect information converting device performs the conversion process to the pixel defect information for non-standard images, and the pixel defect information for non-standard images is stored in the non-standard image defect information storage device, for all of the non-standard radiographic images. Therefore, after the pixel defect information for standard images is stored, the storing of the pixel defect information for non-standard images can be completed promptly for all of the non-standard radiographic images.

Preferably, in the radiographic apparatus according to this invention, after the radiographic mode designating device designates the non-standard radiographic mode, the pixel defect information converting device converts the pixel defect information for standard images into pixel defect information for non-standard images corresponding to the non-standard radiographic images in the non-standard radiographic mode designated by the radiographic mode designating device, and inputs the pixel defect information for non-standard images to the signal correcting device.

The following functional effect is produced by this example where, after the non-standard radiographic mode is designated, the conversion is made to pixel defect information for non-standard images, which is inputted to the signal correcting device. That is, after the radiographic mode designating device designates the non-standard radiographic mode, the pixel defect information converting device converts the pixel defect information for standard images into pixel defect information for non-standard images. This conversion from the pixel defect information for standard images to the pixel defect information for non-standard images is a real-time conversion. As a result, the latest pixel defect information for standard images is always reflected on the pixel defect information for non-standard images. Further, since the pixel defect information for non-standard images is inputted to the signal correcting device from the pixel defect information converting device, there is no need to store the pixel defect information for non-standard images in memory.

Specific examples of the radiographic mode designating device in the radiographic apparatus according to this invention include the following:

For example, the radiographic mode designating device may be arranged to designate a non-standard radiographic mode for acquiring non-standard radiographic images with a plurality of the radiation detecting elements clustered and assigned to each pixel.

In this example, when the radiographic mode designating device designates the non-standard radiographic mode for acquiring non-standard radiographic images with a plurality of the radiation detecting elements clustered and assigned to each pixel, non-standard radiographic images are acquired as having each pixel formed of radiation detecting signals from a plurality of the radiation detecting elements.

In another example, the radiographic mode designating device is arranged to designate a non-standard radiographic mode for acquiring non-standard radiographic images with radiation detecting elements in a limited matrix range assigned to the respective pixels.

In this example, when the radiographic mode designating device designates the non-standard radiographic mode for acquiring non-standard radiographic images with radiation detecting elements in a limited matrix range assigned to the respective pixels, non-standard radiographic images are acquired, each being formed only of radiation detecting signals from a plurality of the radiation detecting elements in the limited matrix range.

In a further example, the radiographic mode designating device is arranged to designate a non-standard radiographic mode for acquiring non-standard radiographic images with radiation detecting elements selected at particular intervals for assignment to the respective pixels.

In this example, when the radiographic mode designating device designates the non-standard radiographic mode for acquiring non-standard radiographic images with radiation detecting elements selected at particular intervals for assignment to the respective pixels, non-standard radiographic images are acquired, each being formed only of radiation detecting signals from the radiation detecting elements selected at the particular intervals.

One example of the two-dimensional radiation detector in the radiographic apparatus according to this invention a flat panel type two-dimensional X-ray detector having numerous X-ray detecting elements arranged in a crisscross pattern on an X-ray detecting surface.

In another aspect of the invention, a radiation detection signal processing method is provided for processing radiation detection signals from a two-dimensional radiation detector having a plurality of radiation detecting elements arranged in a two-dimensional matrix, the method comprising the steps of checking a signal strength of each radiation detection signal, and determining presence or absence of a defect in each radiation detecting element; storing results of determination as pixel defect information for standard images; and performing a conversion process for converting the pixel defect information for standard images into pixel defect information for non-standard images; wherein the pixel defect information for standard images is defect information containing, in an element-to-pixel relationship, presence or absence of defects in the radiation detecting elements corresponding to the respective pixels of the standard radiographic images; the pixel defect information for non-standard images is defect information containing, in an element-to-pixel relationship, presence or absence of defects in the radiation detecting elements corresponding to the respective pixels of the non-standard radiographic images;

the standard radiographic images are images each having a plurality of pixels arranged in the same two-dimensional matrix as the radiation detecting elements, with the radiation detecting elements assigned in a one-to-one relationship to the pixels; the non-standard radiographic images are images for which the radiation detecting elements are assigned to pixels differently from a standard radiographic mode for acquiring the standard radiographic images; and the conversion process for conversion into the pixel defect information for non-standard images includes a defect determining process for checking, based on the pixel defect information for standard images stored, whether even one defective radiation detecting element is present among the detecting elements assigned to the pixels of the non-standard radiographic images, and determining pixels with even one defective detecting element assigned thereto to be "defective", and pixels with no defective detecting element assigned thereto to be "defectless".

The radiation detection signal processing method according to this invention can effectively implement the signal processing including the conversion process in the radiographic apparatus according to the invention.

Preferably, the radiation detection signal processing method according to this invention further comprises a step of storing the pixel defect information for non-standard images resulting from the conversion process.

The method where the pixel defect information for non-standard images is stored can effectively implement the signal processing including the conversion process in the radiographic apparatus that stores the pixel defect information for non-standard images.

Where the pixel defect information for non-standard images is stored, the radiation detection signal processing method according to this invention, preferably, is such that, after the pixel defect information for standard images is stored, the conversion process to the pixel defect information for non-standard images and storing of the pixel defect information for non-standard images are carried out for all of the non-standard radiographic images.

Where the conversion process to the pixel defect information for non-standard images and storing of the pixel defect information for non-standard images are carried out for all of the non-standard radiographic images, the method can effectively implement the signal processing including the conversion process in the radiographic apparatus that performs the described conversion process and storing for all of the non-standard radiographic images.

Preferably, the radiation detection signal processing method according to this invention further comprises the steps of selectively designating the standard radiographic mode for acquiring the standard radiographic images, and a non-standard radiographic mode for acquiring the non-standard radiographic images; and correcting the radiation detection signals according to the pixel defect information for standard images when the standard radiographic mode is designated, and according to the pixel defect information for non-standard images when the non-standard radiographic mode is designated.

The method including the radiographic mode designating step and correcting step can effectively implement the signal processing including the correction process after the conversion process in the radiographic apparatus that performs the described conversion process and storing for all of the non-standard radiographic images.

In a preferred example including the radiographic mode designating step and correcting step, after the non-standard radiographic mode is designated, the pixel defect information for standard images is converted into pixel defect information for non-standard images corresponding to the non-standard radiographic images in the non-standard radiographic mode designated, and the pixel defect information for non-standard images is passed to the signal correcting step.

Where the pixel defect information for non-standard images is obtained and inputted to the signal correcting device after the non-standard radiographic mode is designated, the method can effectively implement the radiographic apparatus that obtains pixel defect information for non-standard images and inputs this information to the signal correcting device after the non-standard radiographic mode is designated.

In one example of signal correction, the pixel values of abnormal radiation detection signals are replaced with pixel values of surrounding normal radiation detection signals. In another example of signal correction, the pixel values of abnormal radiation detection signals are replaced with interpolation values calculated by using pixel values of normal radiation detection signals adjacent the abnormal signals.

On example of the non-standard radiographic images is a cluster radiographic image with a plurality of the radiation detecting elements clustered and assigned to each pixel. Another example of the non-standard radiographic images is a limited radiographic image with radiation detecting elements in a limited matrix range assigned to the respective pixels. A further example of the non-standard radiographic images is a thin-out radiographic image with radiation detecting elements selected at particular intervals for assignment to the respective pixels.

BRIEF DESCRIPTION OF THE DRAWINGS

For the purpose of illustrating the invention, there are shown in the drawings several forms which are presently preferred, it being understood, however, that the invention is not limited to the precise arrangement and instrumentalities shown.

DESCRIPTION OF THE PREFERRED EMBODIMENTS

Preferred embodiments of this invention will be described in detail hereinafter with reference to the drawings.

First Embodiment

Figure 1:
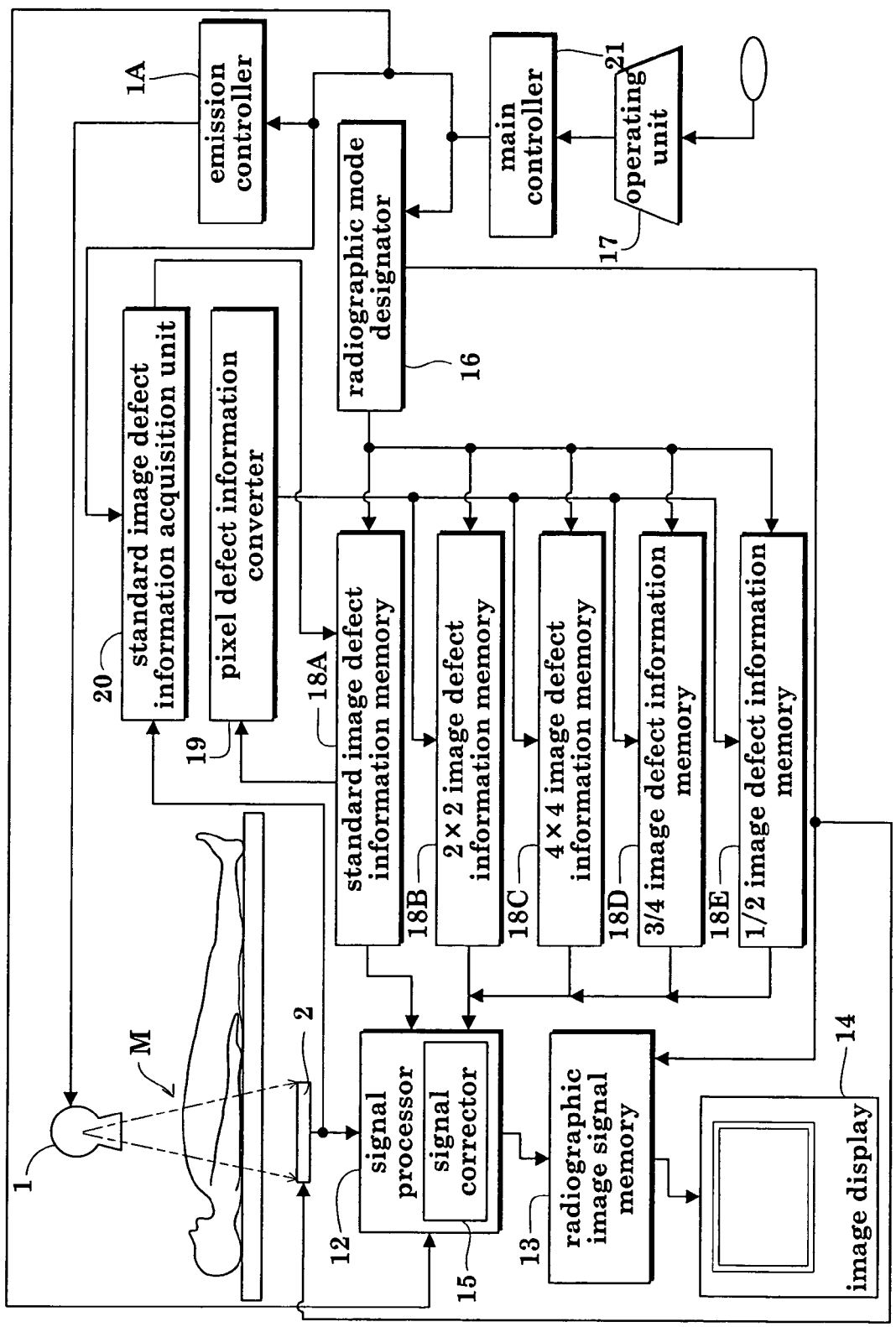
FIG. 1 is a block diagram showing an overall construction of an X-ray imaging apparatus in a first embodiment.

A first embodiment of this invention will be described with reference to the drawings. FIG. 1 is a block diagram showing an overall construction of an X-ray imaging apparatus (radiographic apparatus) in the first embodiment.

Figure 8:
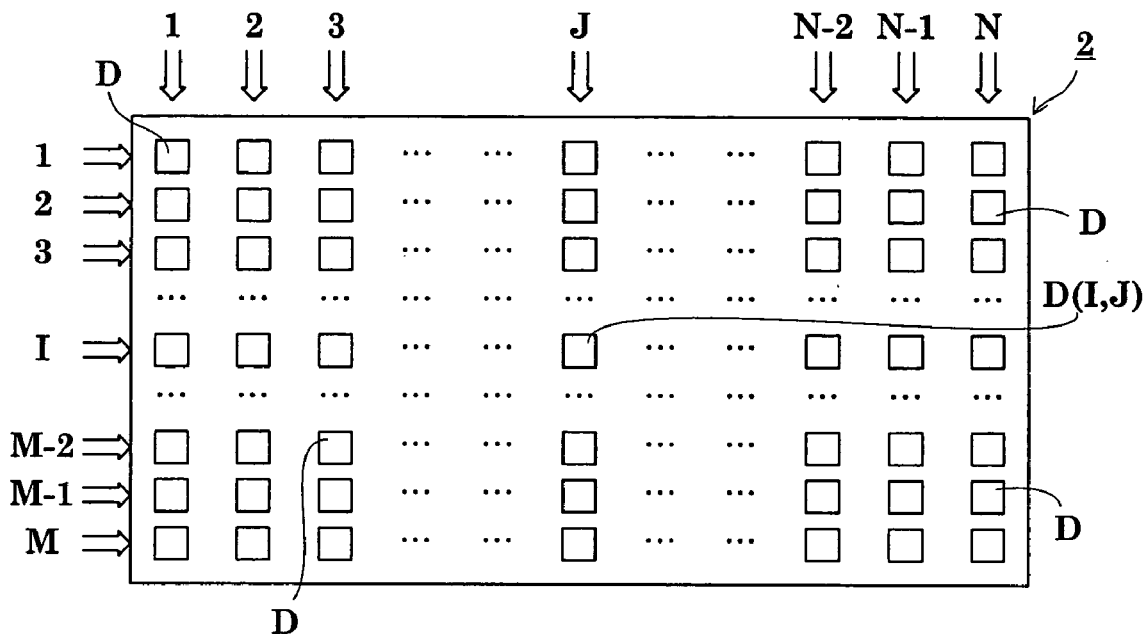
FIG. 8 is a schematic view showing a two-dimensional matrix arrangement of radiation detecting elements on an FPD.

The X-ray imaging apparatus in the first embodiment shown in FIG. 1 includes an X-ray tube 1 for emitting X rays as radiation to a patient M to be radiographed, and a flat panel type two-dimensional X-ray detector (hereinafter called "FPD" as appropriate) 2. As shown in FIG. 8, the FPD 2 has radiation detecting elements D arranged in a two-dimensional matrix of M rows and N columns, and thus M×N detecting elements D, on a radiation detecting surface. The X-ray tube 1 and FPD 2 are constantly opposed to each other across the patient M. When the X-ray tube 1, under control of an emission controller 1A, emits X rays to the patient M, a transmitted X-ray image of the patient M is projected to the radiation detecting surface of FPD 2. The X-ray tube 1 corresponds to the radiation emitting device in this invention. The FPD 2 corresponds to the two-dimensional radiation detector in this invention.

Figure 9:
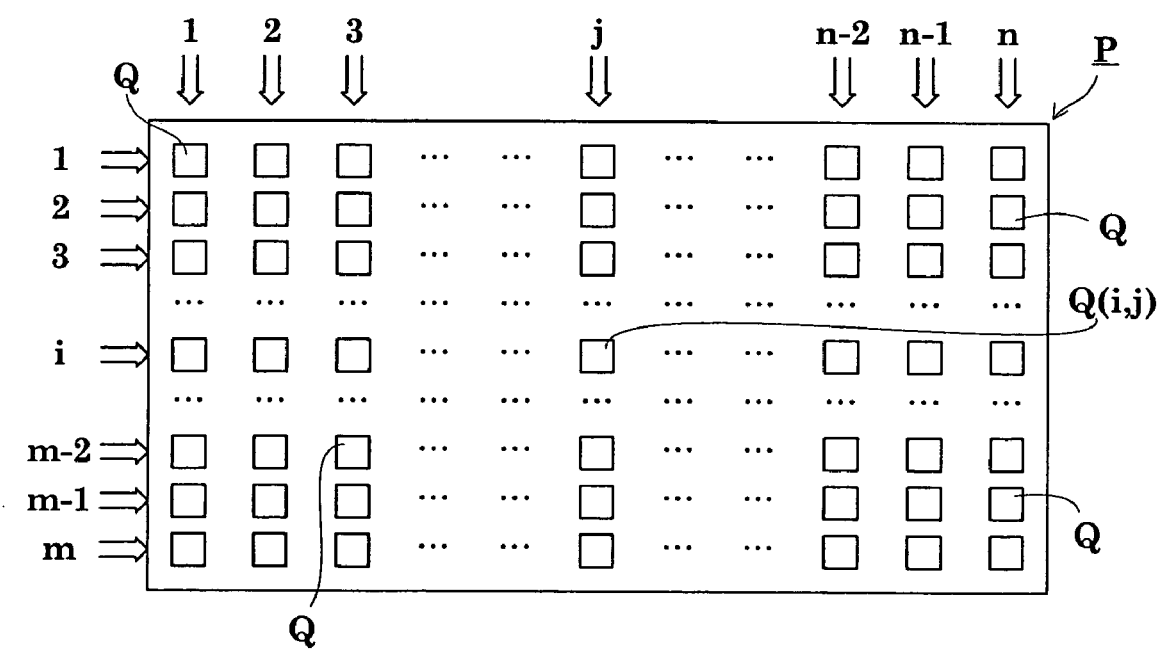
FIG. 9 is a schematic view showing a two-dimensional matrix arrangement of pixels in an X-ray image.

During X-ray radiography, the X-ray tube 1 emits X rays to the patient M, and the FPD 2 detects a transmitted X-ray image of patient M. The FPD 2 outputs X-ray detection signals for creating an X-ray image P which, as shown in FIG. 9, has m×n pixels Q arranged in a two-dimensional matrix of m rows and n columns. The X-ray image P corresponds to a radiographic image in this invention.

The FPD 2 is a direct conversion type X-ray detector having radiation detecting elements D arranged in a two-dimensional matrix of 2,048 (=M) rows and 2,048 (=N) columns on a radiation detecting surface about 30 to 50 cm long and 30 to 50 cm wide, for example.

Figure 2:
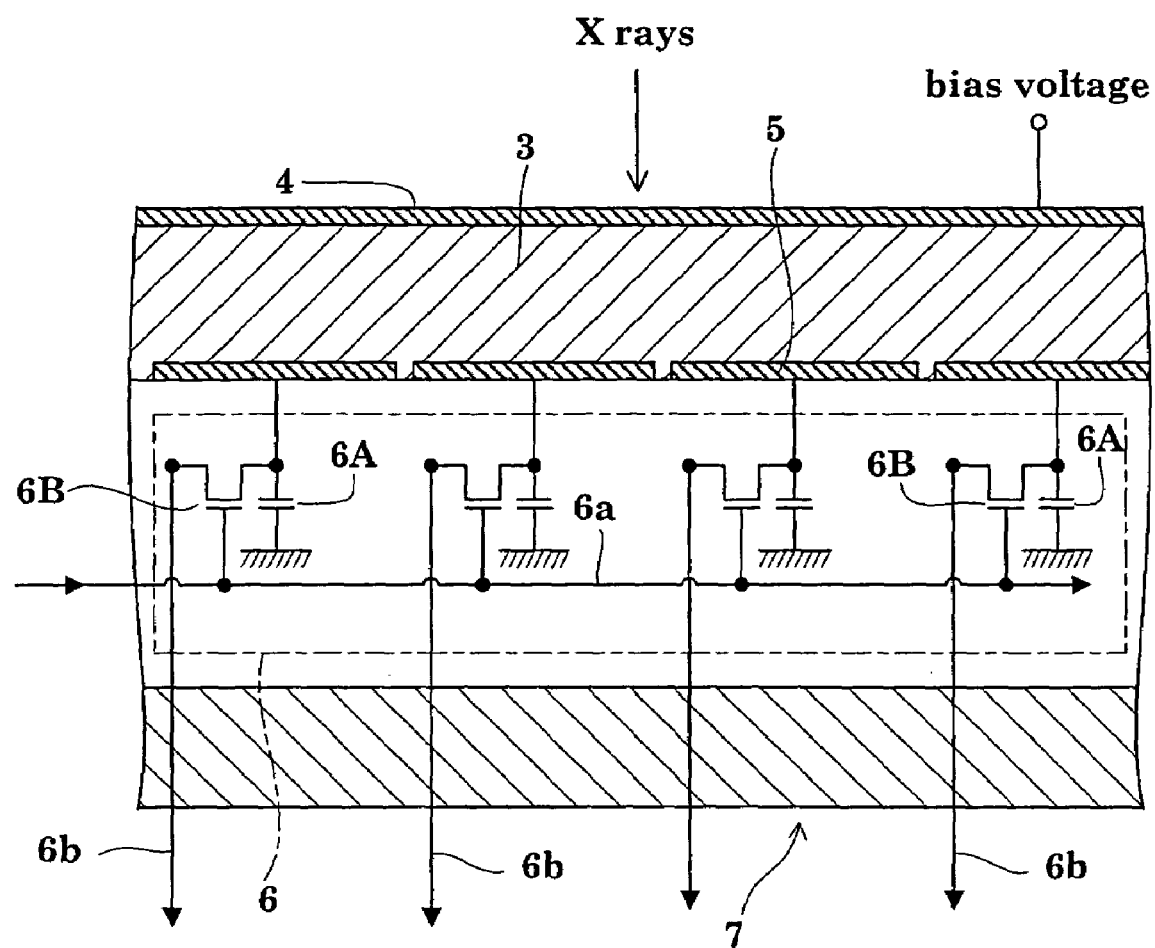
FIG. 2 is a schematic sectional view showing a construction of an FPD centering on an X-ray sensor portion.
Figure 3:
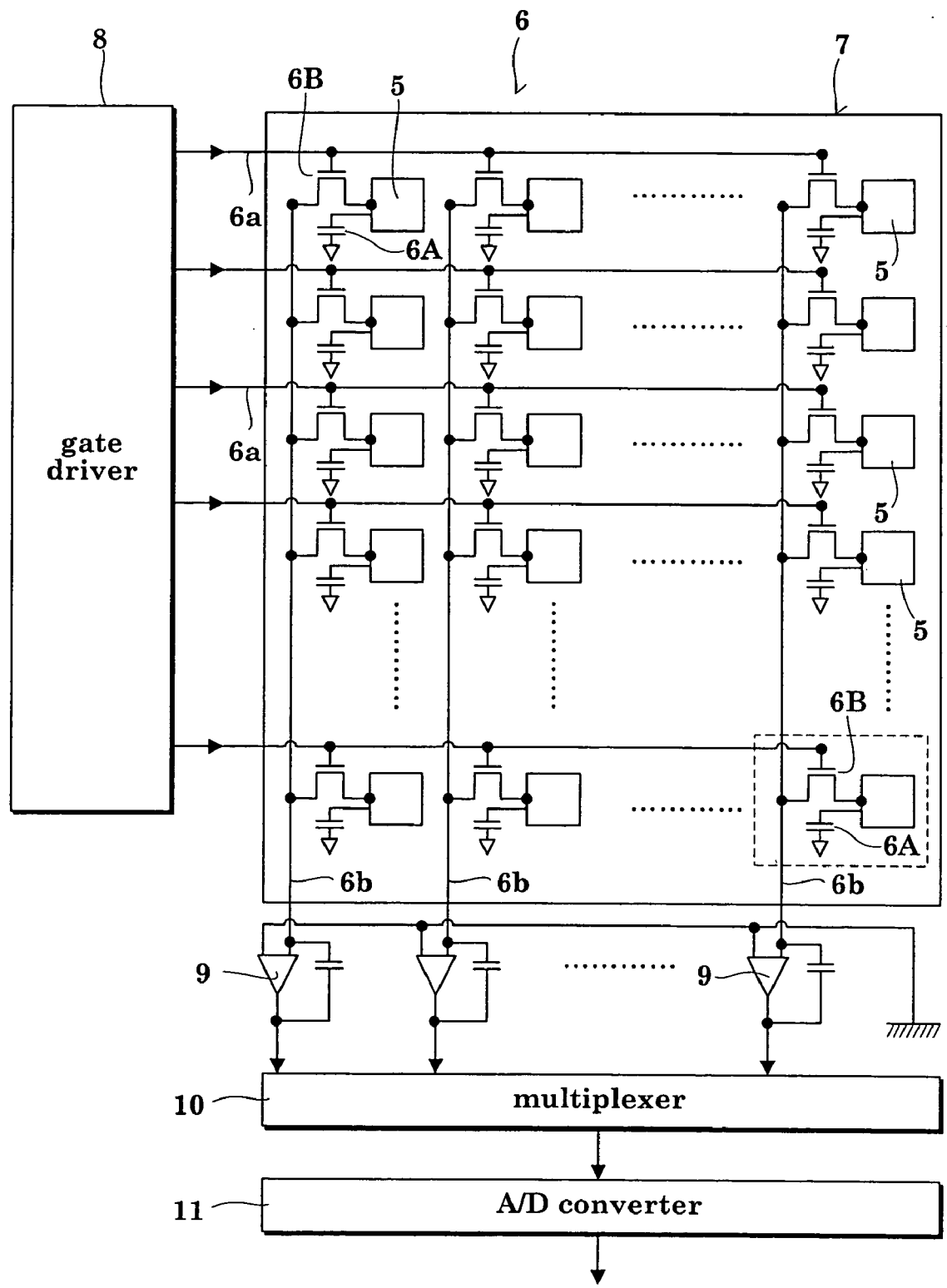
FIG. 3 is a block diagram showing the construction of the FPD centering on a detection signal reading circuit.

As shown in FIG. 2, the FPD 2 includes a radiation sensitive member 3 such as an a-Se semiconductor film for converting incident X rays directly into electric charges, a common electrode 4 for bias voltage application laminated in a planar form on the surface of the radiation sensitive member 3, and an active matrix substrate 7 having an electric circuit 6 arranged thereon for storing and reading electric charges collected by individual electrodes 5. As shown in FIG. 3, the active matrix substrate 7 has numerous individual electrodes 5 formed in the two-dimensional matrix arrangement of radiation detecting elements D on the surface of the substrate 7, with the above storage and reading electric circuit 6 also arranged thereon. The above radiation sensitive member 3 is laminated on the surface of the active matrix substrate 7 where the individual electrodes 5 are formed.

The storage and reading electric circuit 6 includes capacitors 6A, TFTs (thin film field effect transistors) 6B acting as switching elements, and electric lines 6a and 6b.

One capacitor 6A and one TFT 6B are assigned to each electrode 5.

As shown in FIG. 3, the storage and reading electric circuit 6 is surrounded by and connected to a gate driver 8, charge-to-voltage conversion type amplifiers 9, a multiplexer 10 and an analog-to-digital converter 11 provided as separate devices.

For the FPD 2 to detect X rays, a bias voltage is applied from the common electrode 4 to the radiation sensitive member 3, and the radiation sensitive member 3 generates electric charges in response to an incidence of X rays to be detected. The electric charges generated by the radiation sensitive member 3 are collected by the individual electrodes 5. More particularly, by movement to the individual electrodes 5, electric charges are induced in each individual electrode 5. The electric charges collected in the individual electrodes 5 are fetched, as distinguished from one another, by the storage and reading electric circuit 6 on the active matrix substrate 7.

Specifically, the gate driver circuit 8 successively applies read signals via electric lines 6a to the gates of the respective TFTs 6B, and the electric lines 6b connected to the sources of the respective TFTs 6B, to which the read signals are applied, are successively switched and connected through the charge-to-voltage conversion type amplifiers 9 to the multiplexer 10. With such switching connection, the charges stored in the capacitors 6A are transmitted from the TFTs 6B through the electric lines 6b to the charge-to-voltage conversion type amplifiers 9 to be amplified therein. The charges amplified are transmitted, separately for each individual electrode 5, by the multiplexer 10 to the analog-to-digital converter 11 to be digitized therein and outputted as X-ray detection signals from the respective radiation detecting elements D.

That is, in the FPD 2, each radiation detecting element D is formed of one individual electrode 5, portions corresponding to the area of the individual electrode 5 of the radiation sensitive member 3 and common electrode 4, one capacitor 6A and one TFT 6B. Output or reading of the X-ray detection signals from the FPD 2 progresses in order from left-hand radiation detecting element D to right-hand detecting element D along each horizontal line. After one horizontal line, the operation moves to a next horizontal line and reads the X-ray detection signals similarly. This process is repeated for one horizontal line after another.

The X-ray imaging apparatus includes, arranged downstream of the FPD 2, a signal processor 12 for performing processes required for X-ray image acquisition on the X-ray detection signals outputted from the FPD 2, a radiographic image signal memory 13 for storing X-ray images, and an image display 14 for displaying the X-ray images. The signal processor 12 acquires X-ray images from the X-ray detection signals outputted from the FPD 2 in response to an emission of X rays from the X-ray tube 1 to the patient M. The X-ray images acquired are stored in the radiographic image signal memory 13. The X-ray images acquired and stored are displayed on the screen of the image display 14. The signal processor 12 performs processes including an offset amendment and sensitivity correction of the X-ray detection signals, for example.

On the one hand, the FPD 2, although lightweight and thin compared with an image intensifier, inevitably includes radiation detecting elements D with defects resulting from a manufacturing process or the like. X-ray detection signals corresponding to the defective radiation detecting elements D are abnormal signals without proper pixel values (signal strength), and will produce defective pixels in the X-ray image P. Thus, in the apparatus in the first embodiment, the signal processor 12 includes a signal corrector 15 for correcting the abnormal X-ray detection signals in real time by replacing the pixel values of each abnormal X-ray detection signal with the pixel values of surrounding normal X-ray detection signals, or with interpolation values calculated by using the pixel values of normal X-ray detection signals adjacent the abnormal signal. The signal corrector 15 corresponds to the signal correcting device in this invention.

On the other hand, the X-ray imaging apparatus in the first embodiment includes a radiographic mode designator 16 for selecting and designating a desired one of a standard radiographic mode and non-standard radiographic modes. The "standard radiographic mode" refers to a mode for acquiring standard X-ray images. The "non-standard radiographic mode" refers to a mode for acquiring non-standard X-ray images.

A "standard X-ray image" has M×N (i.e. 2,048×2,048) pixels Q (i, j) arranged in the same two-dimensional matrix as the radiation detecting elements D, with the radiation detecting elements D (I, J) assigned in a one-to-one relationship to the pixels Q (i, j). A "non-standard X-ray image" refers to an image having pixels Q (i, j) to which the radiation detecting elements D (I, J) are assigned differently from the standard radiographic mode. The standard X-ray image corresponds to the standard radiographic image in this invention. The non-standard X-ray image corresponds to the non-standard radiographic image in this invention. The radiographic mode designator 16 corresponds to the radiographic mode designating device in this invention.

The non-standard radiographic modes designated by the radiographic mode designator 16 include a cluster radiographic mode and a limited radiographic mode. The "cluster radiographic mode" is a mode for acquiring cluster X-ray images (non-standard X-ray images) with a plurality of radiation detecting elements D clustered and assigned to each pixel Q. The "limited radiographic mode" refers to a mode for acquiring limited X-ray images (non-standard X-ray images) with radiation detecting elements D in a certain limited matrix range assigned to the pixels Q.

In the cluster radiographic mode, non-standard X-ray images are acquired with each pixel Q formed of X-ray detection signals from a plurality of radiation detecting elements D. In the limited radiographic mode, non-standard X-ray images are acquired, each formed of X-ray detection signals from radiation detecting elements D in a limited matrix range.

The standard radiographic mode is suitable for obtaining high definition X-ray images, for example. The cluster radiographic mode is suitable for obtaining low-dose X-ray images, such as for fluoroscopic purposes. The limited radiographic mode is suitable for obtaining size conversion images or limited field images, for example.

Each radiographic mode may be selected by using an operating unit 17 including input devices such as a mouse and a keyboard.

Figure 4A:
FIG. 4A is a schematic view showing a way in which radiation detecting elements are clustered in a cluster radiographic mode of the apparatus in the first embodiment.
Figure 4A:
Figure 4B:
FIG. 4B is a schematic view showing another way in which the radiation detecting elements are clustered in the clustered radiographic mode of the apparatus in the first embodiment.
Figure 4B:
Figure 4B:
Figure 4B:

One specific example of the cluster radiographic mode is a 2×2 cluster radiographic mode for acquiring 2×2 cluster X-ray images in which a group of four radiation detecting elements D in a 2×2 mini matrix arrangement of two rows and two columns, as shown in FIG. 4A, is assigned to each successive pixel Q. Another example is a 4×4 cluster radiographic mode for acquiring 4×4 cluster X-ray images in which a group of 16 radiation detecting elements D in a 4×4 mini matrix arrangement of four rows and four columns, as shown in FIG. 4B, is assigned to each successive pixel Q.

Thus, in 2×2 cluster X-ray images, each pixel Q is formed of X-ray detection signals from four radiation detecting elements D. In 4×4 cluster X-ray images, each pixel Q is formed of X-ray detection signals from 16 radiation detecting elements D.

Figure 5:
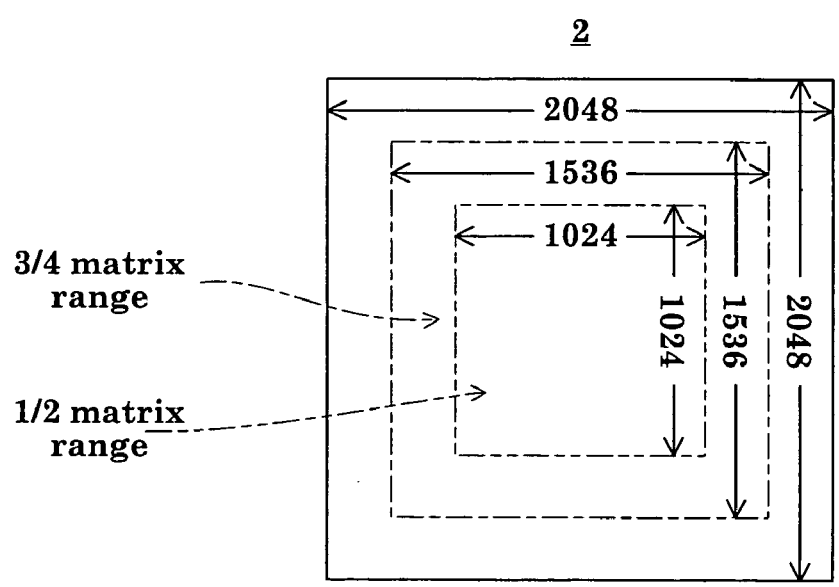
FIG. 5 is a schematic view showing ways of limiting a matrix of element arrangement in a limited radiographic mode of the apparatus in the first embodiment.

One specific example of the limited radiographic mode is a ¾ limited radiographic mode for acquiring ¾ limited X-ray images in which radiation detecting elements D in a matrix range of 1,536×1,536, i.e. ¾ by ¾, as shown in alternate long and short dash lines in FIG. 5, are assigned to the respective pixels Q. Another example is a ½ limited radiographic mode for acquiring ½ limited X-ray images in which radiation detecting elements D in a matrix range of 1,024×1,024, i.e. ½ by ½, as shown in alternate long and two short dashes lines in FIG. 5, are assigned to the respective pixels Q.

Thus, each ¾ limited X-ray image corresponds to a transmitted X-ray image projected to the matrix range of 1,536×1,536 in the center. Each ½ limited X-ray image corresponds to a transmitted X-ray image projected to the matrix range of 1,024×1,024 in the center.

The X-ray imaging apparatus in the first embodiment further includes a standard image defect information memory 18A, a pixel defect information converter 19 and defect information memories 18B–18E. The standard image defect information memory 18A stores pixel defect information for standard images (hereinafter called simply "defect information" where appropriate). This information contains, in an element-to-pixel relationship, the presence or absence of defects in the radiation detecting elements D corresponding to the respective pixels Q of standard X-ray images.

The pixel defect information converter 19 performs a conversion process for converting the standard image pixel defect information into non-standard image pixel defect information (hereinafter called simply "defect information" where appropriate). The defect information memories 18B–18E store, for different non-standard X-ray images, the non-standard image pixel defect information resulting from the conversion process by the pixel defect information converter 19. The standard image defect information memory 18A corresponds to the standard image defect information storage device in this invention. The defect information memories 18B–18E correspond to the non-standard image defect information storage devices in this invention. The pixel defect information converter 19 corresponds to the pixel defect information converting device in this invention.

The conversion process by the pixel defect information converter 19 is performed through the following procedure. Based on the defect information stored in the standard image defect information memory 18A, a checking is made for each pixel Q in a non-standard X-ray image to find out whether even one defective radiation detecting element D is present among the detecting elements D assigned to the pixels Q. Pixels Q with even one defective detecting element D assigned thereto are determined "defective". Pixels Q with no defective detecting element D assigned thereto are determined "defectless". Through such determining procedure, the standard image pixel defect information is converted into non-standard image pixel defect information showing, in an element-to-pixel relationship, the presence or absence of defects in the radiation detecting elements D corresponding to the respective pixels Q in non-standard X-ray images.

The defect information for standard X-ray images is information on all the individual radiation detecting elements D. Consequently, the defect information stored in the standard image defect information memory 18A provides element defect data showing whether or not a defect is present in each of the radiation detecting elements D.

The defect information for standard X-ray images is stored in the standard image defect information memory 18A as follows. First, output signals for defect information acquisition are collected from all the radiation detecting elements D of FPD 2 (e.g. an offset signal of each radiation detecting element). A standard image defect information acquisition unit 20 checks whether the signal strength of each output signal collected for defect information acquisition has an abnormal value or not, thereby to determine the presence or absence of a defect in each radiation detecting element D. The standard image defect information memory 18A stores, as the defect information, results of the determination by the standard image defect information acquisition unit 20.

For a 2×2 cluster X-ray image, the pixel defect information converter 19 refers to the pixel defect data stored in the standard image defect information memory 18A. The converter 19 checks the presence or absence of a defect in each of the four radiation detecting elements D assigned to each pixel Q. The pixel Q is determined defective when even one element D has a defect, and defectless when all the four elements D are found free from defect. The standard image pixel defect information is converted into 2×2 cluster X-ray image pixel defect information showing, in an element-to-pixel relationship, the presence or absence of defects in the radiation detecting elements D corresponding to the respective pixels Q in the 2×2 cluster X-ray image. The defect information memory 18B for 2×2 cluster X-ray images stores the 2×2 cluster X-ray image pixel defect information resulting from the conversion by the pixel defect information converter 19.

For a 4×4 cluster X-ray image also, the pixel defect information converter 19 refers to the pixel defect data stored in the standard image defect information memory 18A. The converter 19 checks the presence or absence of a defect in each of the 16 radiation detecting elements D assigned to each pixel Q. The pixel Q is determined defective when even one element D has a defect, and defectless when all the 16 elements D are found free from defect. The standard image pixel defect information is converted into 4×4 cluster X-ray image pixel defect information showing, in an element-to-pixel relationship, the presence or absence of defects in the radiation detecting elements D corresponding to the respective pixels Q in the 4×4 cluster X-ray image. The defect information memory 18C for 4×4 cluster X-ray images stores the 4×4 cluster X-ray image pixel defect information resulting from the conversion by the pixel defect information converter 19.

For a ¾ limited X-ray image, the pixel defect information converter 19 refers to the pixel defect data stored in the standard image defect information memory 18A. The ¾ limited X-ray image is determined defective when any radiation detecting element D has a defect, and defectless when all the elements D are found free from defect. The standard image pixel defect information is converted into ¾ limited X-ray image pixel defect information showing, in an element-to-pixel relationship, the presence or absence of defects in the radiation detecting elements D corresponding to the respective pixels Q in the ¾ limited X-ray image. The defect information memory 18D for ¾ limited X-ray images stores the ¾ limited X-ray image pixel defect information resulting from the conversion by the pixel defect information converter 19.

For a ½ limited X-ray image also, the pixel defect information converter 19 refers to the pixel defect data stored in the standard image defect information memory 18A. The ½ limited X-ray image is determined defective when any radiation detecting element D has a defect, and defectless when all the elements D are found free from defect. The standard image pixel defect information is converted into ½ limited X-ray image pixel defect information showing, in an element-to-pixel relationship, the presence or absence of defects in the radiation detecting elements D corresponding to the respective pixels Q in the ½ limited X-ray image. The defect information memory 18E for ½ limited X-ray images stores the ½ limited X-ray image pixel defect information resulting from the conversion by the pixel defect information converter 19.

In the apparatus in the first embodiment, after the defect information for standard X-ray images is stored in the standard image defect information memory 18A, the pixel defect information converter 19 determines defects and stores defect information in the other, non-standard X-ray image defect information memories 18B–18E for all non-standard X-ray images.

When the radiographic mode designator 16 designates the standard radiographic mode, the signal corrector refers to the defect information stored in the standard image defect information memory 18A, and corrects the abnormal X-ray detection signal relating to any pixel Q indicated defective. As a result, an X-ray image without a defective pixel is acquired.

When the radiographic mode designator 16 designates the 2×2 cluster radiographic mode, the signal corrector 15 refers to the 2×2 cluster image pixel defect information stored in the 2×2 cluster image defect information memory 18B, and corrects the abnormal X-ray detection signal relating to any pixel Q indicated defective. As a result, an X-ray image without a defective pixel is acquired.

Further, when the 4×4 radiographic mode, ¾ limited radiographic mode or ½ limited radiographic mode is designated, the signal corrector 15 refers to the defect information stored in the 4×4 cluster image defect information memory 18C, ¾ limited image defect information memory 18D or ½ limited image defect information memory 18E, and corrects the abnormal X-ray detection signal relating to any pixel Q indicated defective. As a result, an X-ray image without a defective pixel is acquired.

A main controller 21 has a computer (CPU) and control programs as main components thereof. The main controller 21 controls an overall radiographic operation with control functions to transmit command signals and required data to various working components according to inputs made through the operating unit 17 and progress of radiography.

Figure 6:
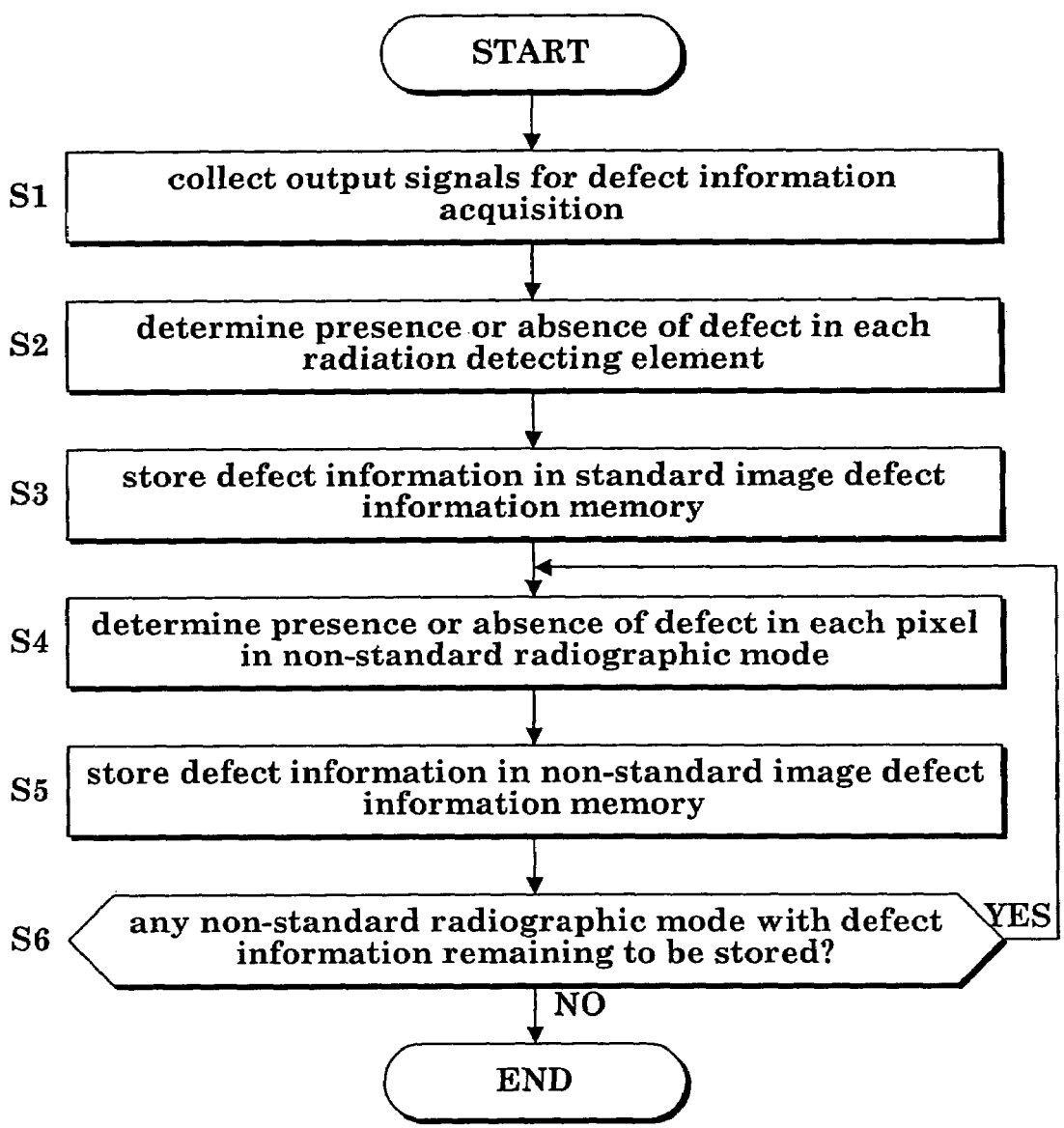
FIG. 6 is a flow chart showing a process of storing defect information in the apparatus in the first embodiment.

Next, a process performed by the above X-ray imaging apparatus when defect information is stored will be described with reference to FIG. 6. FIG. 6 is a flow chart of a defect information storing process in the first embodiment.

[Step S1] Output signals are collected from the FPD 2 for acquiring standard X-ray image pixel defect information to be used in correcting X-ray detection signals for standard X-ray images. The output signals may be offset signals for all the radiation detecting elements, for example.

[Step S2] The standard image defect information acquisition unit 20 checks the signal strength of each output signal collected for defect information acquisition to determine the presence or absence of a defect in each radiation detecting element.

[Step S3] The standard image defect information memory 18A stores, as standard image defect information, results of the determination by the standard image defect information acquisition unit 20.

[Step S4] The pixel defect information converter 19 refers to the element defect data stored in the standard image defect information memory 18A, determines the presence or absence of a defect in each pixel Q in a non-standard X-ray image (e.g. a 2×2 cluster X-ray image) in a first non-standard radiographic mode (e.g. the 2×2 cluster radiographic mode), and converts the standard X-ray image pixel defect information into non-standard X-ray image (e.g. 2×2 cluster X-ray image) pixel defect information.

[Step S5] The defect information memory for non-standard images (e.g. the defect information memory 18B for 2×2 cluster X-ray images) stores the non-standard X-ray image (e.g. 2×2 cluster X-ray image) pixel defect information resulting from the conversion by the pixel defect information converter 19.

[Step S6] If a non-standard radiographic mode for which defect information is not stored remains, the operation returns to step S4 to repeat the conversion and storage of defect information for the remaining non-standard radiographic mode.

If no such non-standard radiographic remains to have defect information stored, it means a completion of the process for storing defect information for all non-standard radiographic modes. Thus, whatever radiographic mode may be designated, the signal corrector 15 is ready to correct X-ray detection signals immediately.

In the X-ray imaging apparatus in the first embodiment, as described above, when the radiographic mode designator 16 designates the standard radiographic mode, the signal corrector 15 refers to the defect information stored in the standard image defect information memory 18A, and corrects abnormal X-ray detection signals, due to defects of the radiation detecting elements D, among the X-ray detection signals outputted from the FPD 2. When the radiographic mode designator 16 designates a non-standard radiographic mode, the signal corrector 15 refers to the defect information stored in one of the non-standard image defect information memories 18B–18E, and corrects abnormal X-ray detection signals, due to defects of the radiation detecting elements D, among the X-ray detection signals outputted from the FPD 2. Since the pixel defect information for non-standard X-ray images is acquired by using the defect information for standard X-ray images, it is unnecessary to collect output signals for pixel defect information acquisition for non-standard X-ray images from the FPD 2 all over again. As a result, when acquiring non-standard X-ray images, abnormal X-ray detection signals due to defects of the radiation detecting elements D may be corrected promptly.

Thus, the apparatus in the first embodiment can promptly correct abnormal X-ray detection signals due to defects of the radiation detecting elements D, regardless of how the radiation detecting elements D are assigned to the pixels Q in X-ray images.

In the apparatus in the first embodiment, pixel defect information for non-standard images to be used for correcting X-ray detection signals for non-standard X-ray images is stored in each of the non-standard image defect information memories 18B-18E. Such pixel defect information for non-standard images may be used without converting the pixel defect information for standard images into pixel defect information for non-standard images. This further speeds up the correction of abnormal radiation detection signals.

Further, in the apparatus in the first embodiment, after storing defect information for standard X-ray images in the standard image defect information memory 18A, the pixel defect information converter 19 determines defects for all non-standard X-ray images, and stores defect information. Thus, after storing defect information for standard X-ray images, the storing of pixel defect information for non-standard images may be completed promptly for all non-standard X-ray images.

Second Embodiment

Figure 7:
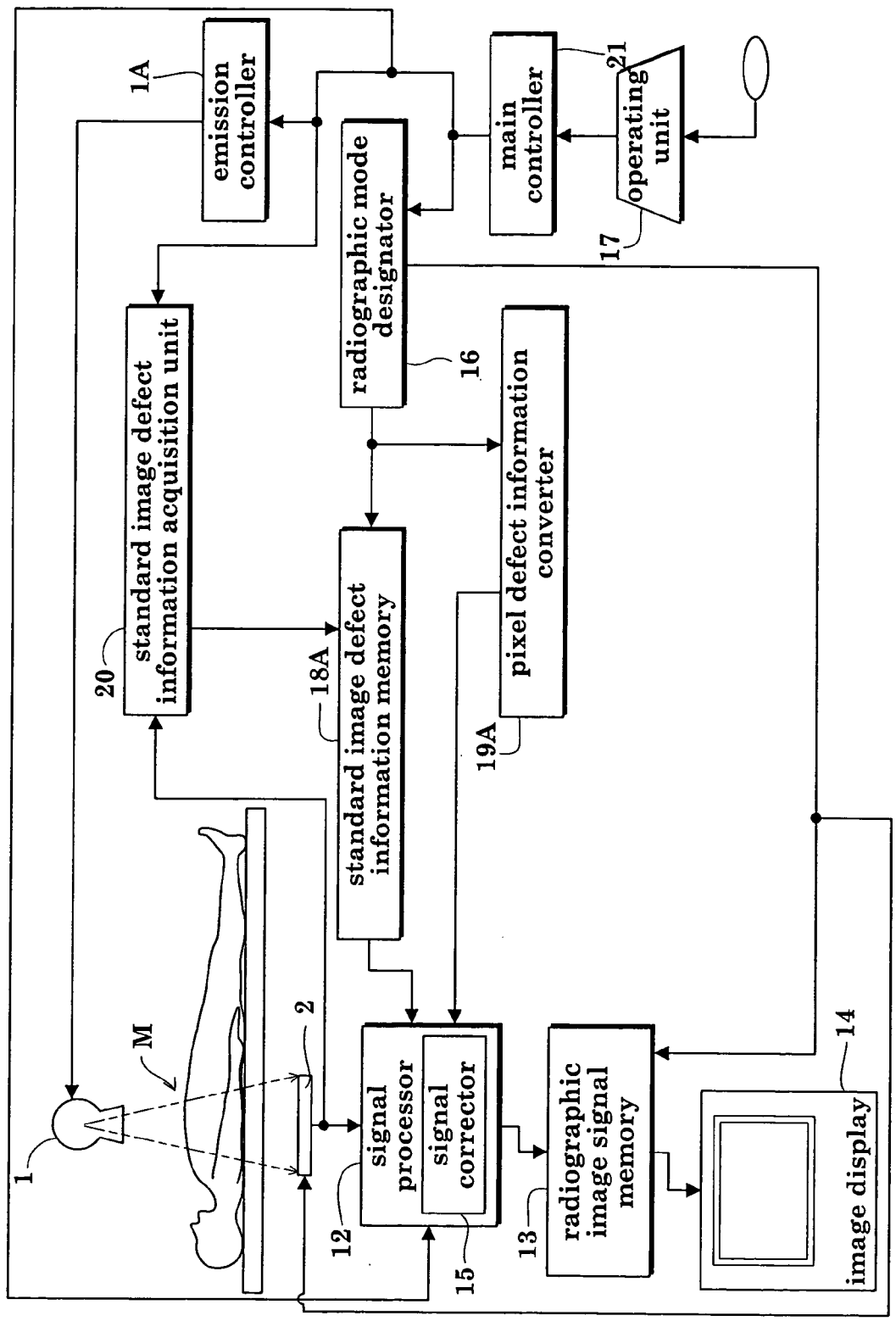
FIG. 7 is a block diagram showing an overall construction of an X-ray imaging apparatus in a second embodiment.

A second embodiment of this invention will be described with reference to FIG. 7. FIG. 7 is a block diagram showing an overall construction of an X-ray imaging apparatus (radiographic apparatus) in the second embodiment. The X-ray imaging apparatus in the second embodiment includes a pixel defect information converter 19A which is substantially the same as its counterpart in the first embodiment except the differences to be described hereinafter. The following description will be made centering on different points, and omitting description of common points in principle. The pixel defect information converter 19A corresponds to the pixel defect information converting device in this invention.

One difference is that, in the second embodiment, after the radiographic mode designator 16 designates a non-standard radiographic mode, the pixel defect information converter 19A converts the pixel defect information for standard images into pixel defect information corresponding to non-standard radiographic images in the non-standard radiographic mode designated by the radiographic mode designator 16, and inputs the pixel defect information to the signal corrector 15. As another different point, the second embodiment does not include the defect information memories 18B–18E.

In the X-ray imaging apparatus in the second embodiment, when the radiographic mode designator 16 designates the standard radiographic mode, the signal corrector 15 corrects abnormal X-ray detection signals according to the pixel defect information for standard images stored in the standard image defect information memory 18A, as in the apparatus in the first embodiment. Thus, standard X-ray images without defective pixels are acquired.

However, when the radiographic mode designator 16 designates a non-standard radiographic mode, the pixel defect information converter 19A determines, based on the pixel defect information for standard images, the presence or absence of a defect in each pixel Q of the non-standard X-ray image (e.g. 2×2 cluster X-ray images) in the non-standard radiographic mode designated by the radiographic mode designator 16. Then, the converter 19A converts the pixel defect information for standard X-ray images into pixel defect information for non-standard X-ray images (e.g. 2×2 cluster X-ray images).

The pixel defect information for non-standard X-ray images resulting from the conversion by the pixel defect information converter 19A is inputted to the signal corrector 15. The signal corrector 15 refers the inputted pixel defect information for non-standard X-ray images, and corrects abnormal X-ray detection signals for non-standard X-ray images (e.g. 2×2 cluster X-ray images). Thus, non-standard X-ray images (e.g. 2×2 cluster X-ray images) without defect pixels are acquired.

In the second embodiment, as noted above, the pixel defect information converter 19A performs a conversion process from the pixel defect information for standard images to the pixel defect information for non-standard images, after a non-standard radiographic mode is designated by the radiographic mode designator 16. The conversion from the pixel defect information for standard images to the pixel defect information for non-standard images is performed in real time. As a result, the latest pixel defect information for standard images is always reflected on the pixel defect information for non-standard images. Further, since the pixel defect information for non-standard images is inputted to the signal corrector 15 from the pixel defect information converter 19A, there is no need to store the pixel defect information for non-standard images in memory. As a result, the second embodiment can dispense with the defect information memories 18B–18E required for the apparatus in the first embodiment.

This invention is not limited to the above embodiments, but may be modified as follows:

(1) In the first embodiment, after the defect information for standard X-ray images is stored, defect information for all non-standard X-ray images is stored. As a modification of this embodiment, after a non-standard radiographic mode is designated, only defect information for non-standard X-ray images relating to the designated non-standard radiographic mode may be stored.

(2) The radiographic mode designator 16 may be modified to designate also a thin-out radiographic mode for acquiring thin-out radiographic images (non-standard radiographic images) with radiation detecting elements D selected at particular intervals for assignment to the respective pixels Q.

(3) In the described embodiments, a 2×2 mini matrix and a 4×4 mini matrix are cited as specific examples of clustering the radiation detecting elements D in the cluster radiographic mode. Such examples are not limitative. For example, the detecting elements D may be clustered in rectangular mini matrices such as a 2×3 mini matrix and a 3×2 mini matrix.

(4) In the described embodiments, a matrix range of ¾ rows by ¾ columns and a matrix range of ½ rows by ½ columns are cited as specific examples of limiting the matrix arrangement of the radiation detecting elements D for the limited radiographic mode. Such examples are not limitative. For example, the detecting elements D may be limited to rectangular matrices such as a matrix range of ¾ rows by ½ columns and a matrix range of ½ rows and ¾ columns.

(5) In the described embodiments, the FPD 2 is a detector of the direct conversion type. The invention is applicable also to an FPD of the indirect conversion type and to a two-dimensional radiation detector other than the FPD. (6) The foregoing embodiments use X rays as radiation. The invention is applicable also to apparatus using radiation other than X rays.

(7) The apparatus in the foregoing embodiments are used for medical purposes. The invention is applicable also to apparatus for industrial or nuclear use.

This invention may be embodied in other specific forms without departing from the spirit or essential attributes thereof and, accordingly, reference should be made to the appended claims, rather than to the foregoing specification, as indicating the scope of the invention.

What is claimed is:

1. A radiographic apparatus having (A) radiation emitting means for emitting radiation to an object to be radiographed, and (B) a two-dimensional radiation detector with a plurality of radiation detecting elements arranged in a two-dimensional matrix, said apparatus comprising:
   (C) radiographic mode designating means for selectively designating a standard radiographic mode for acquiring standard radiographic images, and a non-standard radiographic mode for acquiring non-standard radiographic images;
   (D) standard image defect information storage means for storing pixel defect information for standard images;
   (E) pixel defect information converting means for performing a conversion process to convert the pixel defect information for standard images stored in said standard image defect information storage means into pixel defect information for non-standard images; and
   (F) signal correcting means for correcting radiation detection signals according to the pixel defect information for standard images when the standard radiographic mode is designated by the radiographic mode designating means, and according to the pixel defect information for non-standard images when the non-standard radiographic mode is designated by the radiographic mode designating means;
   wherein said standard radiographic images are images each having a plurality of pixels arranged in the same two-dimensional matrix as the radiation detecting elements, with the radiation detecting elements assigned in a one-to-one relationship to the pixels;
   said non-standard radiographic images are images for which the radiation detecting elements are assigned to pixels differently from the standard radiographic mode;
   said pixel defect information for standard images is defect information containing, in an element-to-pixel relationship, presence or absence of defects in the radiation detecting elements corresponding to the respective pixels of the standard radiographic images;
   said pixel defect information for non-standard images is defect information containing, in an element-to-pixel relationship, presence or absence of defects in the radiation detecting elements corresponding to the respective pixels of the non-standard radiographic images; and
   said conversion process by said pixel defect information converting means for conversion into said pixel defect information for non-standard images includes a defect determining process for checking, based on the pixel defect information for standard images stored in said standard image defect information storage means, whether even one defective radiation detecting element is present among the detecting elements assigned to the pixels of the non-standard radiographic images, and determining pixels with even one defective detecting element assigned thereto to be "defective", and pixels with no defective detecting element assigned thereto to be "defectless".

2. A radiographic apparatus as defined in claim 1, further comprising:
   (G) non-standard image defect information storage means for storing said pixel defect information for non-standard images resulting from the conversion process by said pixel defect information converting means;
   wherein said signal correcting means is arranged to correct said radiation detection signals according to the pixel defect information for non-standard images stored in said non-standard image defect information storage means.

3. A radiographic apparatus as defined in claim 2, wherein, after said pixel defect information for standard images is stored in said standard image defect information storage means, said pixel defect information converting means performs said conversion process to said pixel defect information for non-standard images, and the pixel defect information for non-standard images is stored in said non-standard image defect information storage means, for all of said non-standard radiographic images.

4. A radiographic apparatus as defined in claim 2, wherein, after said radiographic mode designating means designates said non-standard radiographic mode, only said pixel defect information for non-standard images relating to said non-standard radiographic mode designated is stored in said non-standard image defect information storage means.

5. A radiographic apparatus as defined in claim 1, wherein, after said radiographic mode designating means designates said non-standard radiographic mode, said pixel defect information converting means converts said pixel defect information for standard images into pixel defect information for non-standard images corresponding to said non-standard radiographic images in the non-standard radiographic mode designated by the radiographic mode designating means, and inputs said pixel defect information for non-standard images to said signal correcting means.

6. A radiographic apparatus as defined in claim 1, wherein said radiographic mode designating means is arranged to designate a non-standard radiographic mode for acquiring non-standard radiographic images with a plurality of said radiation detecting elements clustered and assigned to each pixel.

7. A radiographic apparatus as defined in claim 1, wherein said radiographic mode designating means is arranged to designate a non-standard radiographic mode for acquiring non-standard radiographic images with radiation detecting elements in a limited matrix range assigned to the respective pixels.

8. A radiographic apparatus as defined in claim 1, wherein said radiographic mode designating means is arranged to designate a non-standard radiographic mode for acquiring non-standard radiographic images with radiation detecting elements selected at particular intervals for assignment to the respective pixels.

9. A radiographic apparatus as defined in claim 1, wherein said two-dimensional radiation detector is a flat panel type two-dimensional X-ray detector having numerous X-ray detecting elements arranged in a crisscross pattern on an X-ray detecting surface.

10. A radiation detection signal processing method for processing radiation detection signals from a two-dimensional radiation detector having a plurality of radiation detecting elements arranged in a two-dimensional matrix, said method comprising the steps of
checking a signal strength of each radiation detection signal, and determining presence or absence of a defect in each radiation detecting element;
storing results of determination as pixel defect information for standard images; and
performing a conversion process for converting the pixel defect information for standard images into pixel defect information for non-standard images;
wherein said pixel defect information for standard images is defect information containing, in an element-to-pixel relationship, presence or absence of defects in the radiation detecting elements corresponding to the respective pixels of the standard radiographic images;
said pixel defect information for non-standard images is defect information containing, in an element-to-pixel relationship, presence or absence of defects in the radiation detecting elements corresponding to the respective pixels of the non-standard radiographic images;
said standard radiographic images are images each having a plurality of pixels arranged in the same two-dimensional matrix as the radiation detecting elements, with the radiation detecting elements assigned in a one-to-one relationship to the pixels;
said non-standard radiographic images are images or which the radiation detecting elements are assigned to pixels differently from a standard radiographic mode for acquiring said standard radiographic images; and
said conversion process for conversion into said pixel defect information for non-standard images includes a defect determining process for checking, based on said pixel defect information for standard images stored, whether even one defective radiation detecting element is present among the detecting elements assigned to the pixels of the non-standard radiographic images, and determining pixels with even one defective detecting element assigned thereto to be "defective", and pixels with no defective detecting element assigned thereto to be "defectless".

11. A radiation detection signal processing method as defined in claim 10, further comprising a step of storing said pixel defect information for non-standard images resulting from said conversion process.

12. A radiation detection signal processing method as defined in claim 11, wherein, after said pixel defect information for standard images is stored, said conversion process to said pixel defect information for non-standard images and storing of the pixel defect information for non-standard images are carried out for all of said non-standard radiographic images.

13. A radiation detection signal processing method as defined in claim 10, further comprising the steps of:
selectively designating the standard radiographic mode for acquiring said standard radiographic images, and a non-standard radiographic mode for acquiring said non-standard radiographic images; and
correcting the radiation detection signals according to the pixel defect information for standard images when the standard radiographic mode is designated, and according to the pixel defect information for non-standard images when the non-standard radiographic mode is designated.

14. A radiation detection signal processing method as defined in claim 13, wherein, after said non-standard radiographic mode is designated, said pixel defect information for standard images is converted into pixel defect information for non-standard images corresponding to said non-standard radiographic images in the non-standard radiographic mode designated, and said pixel defect information for non-standard images is passed to said signal correcting step.

15. A radiation detection signal processing method as defined in claim 10, wherein said signal correcting step is executed to replace pixel values of abnormal radiation detection signals with pixel values of surrounding normal radiation detection signals.

16. A radiation detection signal processing method as defined in claim 10, wherein said signal correcting step is executed to replace pixel values of abnormal radiation detection signals with interpolation values calculated by using pixel values of normal radiation detection signals adjacent the abnormal signals.

17. A radiation detection signal processing method as defined in claim 10, wherein said non-standard radiographic images are cluster radiographic images with a plurality of said radiation detecting elements clustered and assigned to each pixel.

18. A radiation detection signal processing method as defined in claim 10, wherein said non-standard radiographic images are limited radiographic images with radiation detecting elements in a limited matrix range assigned to the respective pixels.

19. A radiation detection signal processing method as defined in claim 10, wherein said non-standard radiographic images are thin-out radiographic images with radiation detecting elements selected at particular intervals for assignment to the respective pixels.

* * * * *